United States Patent [19]
Kim

[11] Patent Number: 4,815,455
[45] Date of Patent: Mar. 28, 1989

[54] PELVIC DISRUPTION REDUCTION ENABLING DEVICE

[75] Inventor: William C. Kim, Westlake Village, Calif.

[73] Assignee: Research and Education Institute, Inc. Harbor-UCLA Medical Center, Torrance, Calif.

[21] Appl. No.: 101,122

[22] Filed: Sep. 21, 1987

Related U.S. Application Data

[63] Continuation of Ser. No. 732,672, May 10, 1985, abandoned.

[51] Int. Cl.$^4$ .............................................. A61F 5/04
[52] U.S. Cl. .............................. 128/92 Z; 128/92 ZZ; 128/92 ZW
[58] Field of Search ................ 128/92 Z, 92 B, 92 C, 128/92 ZZ, 92 ZY, 92 ZK, 92 ZW

[56] References Cited

U.S. PATENT DOCUMENTS

| | | | |
|---|---|---|---|
| 2,391,537 | 12/1945 | Anderson | 128/92 Z |
| 3,990,438 | 11/1976 | Pritchard | 128/92 BC |
| 4,098,269 | 7/1978 | Jodet | 128/92 Z |
| 4,135,505 | 1/1979 | Day | 128/92 Z |
| 4,456,005 | 6/1984 | Lichty | 128/92 B |
| 4,485,542 | 12/1984 | Helland | 128/92 ZZ |
| 4,628,922 | 12/1986 | Dewar | 128/92 ZW |
| 4,662,365 | 5/1987 | Gotzen et al. | 128/92 ZW |

Primary Examiner—Robert A. Hafer
Assistant Examiner—Kevin G. Rooney
Attorney, Agent, or Firm—Drucker & Sommers

[57] ABSTRACT

A device for enabling substantially-anatomic reduction of a posteriorly unstable pelvic disruption, as of a fracture or dislocation of the posterior pelvis. The device is adapted to enable secure fixation thereof to the posterior pelvic disruption. It is further adapted to enable fine adjustment of the alignment and fit of the disrupted surfaces, operable from a position externally of the patient's body, and to retain the united positions of the disrupted surfaces, for substantially-anatomically reducing the posteriorly unstable pelvic disruption. The device includes a plurality of tapper threaded pins, each adapted to be tapped into the outer cortices of the posterior pelvic bone at a location proximate the site of the posterior pelvic disruption. The device further includes a frame, adapted to enable the tapper threaded pins to be connected thereto for interconnection thereof, and mechanisms adapted to enable externally operable fine adjustment of the frame in a plurality of planes. The mechanisms of the frame are operable to apply compressive force, through the tapper threaded pins, connected to such mechanisms and securely affixed to the posterior pelvis, to the pelvic disruption surfaces, to compress and unite such surfaces into close well-fitting substantially anatomic engagement, and to retain the aligned and united positions of the disrupted surfaces.

7 Claims, 2 Drawing Sheets

4,815,455

PELVIC DISRUPTION REDUCTION ENABLING DEVICE

This application is a continuation of application Ser. No. 732,672, filed May 10, 1985, abandoned.

BACKGROUND OF THE INVENTION

The invention relates generally to devices for correcting fractures or the like. It relates specifically to such a device adapted to enable substantially-anatomic reduction of a posteriorly unstable pelvic disruption.

The prior art includes pins for use in reducing bone disruptions, as in U.S. Pat. Nos. 4,175,555 and 3,977,138. Such pins include threaded ends for enabling tapping thereof into portions of the bone in which the disruption has occured, at locations spaced about the disrupted surfaces.

Such pins are adapted to enable holding of the portions of the disrupted bone to which they are secured, in compressive engagement, for reducing the fracture. However, such pins are not adapted to enable secure fixation thereof for securely holding portions of a large bone, as the posterior pelvis, in compressive engagement, to enable reduction of a posteriorly unstable pelvic fracture The prior art further includes frames for use in reducing bone fractures or disruptions, as in U.S. Pat. Nos. 2,250,417 and 4,398,898. However, such frames are likewise not adapted for use in reducing fractures of large bones, as the posterior pelvis.

The prior art still further includes frames adapted for use in reducing pelvic fractures, as in U.S. Pat. Nos. 4,361,144, 4,024,860, and 4,185,623. However, such frames are secureable to the anterior pelvis, a relatively small non-weight bearing portion of the pelvic bone. Further, such frames require a multiplicity of relatively thin pins for securing thereof to the anterior pelvis, and include complex and inefficient mechanisms for applying compressive force therethrough to the fractured bone for reducing the fracture.

Further, such anterior frames are adapted for use in reducing pelvic disruptions where satisfactory stability may be achieved by anterior pelvic fixation, as where supporting ligaments are functionally intact and where there is no posterior instability. Such frames and pins are further generally not strong enough to permit prompt patient ambulation and sitting, thereby requiring prolonged patient bed rest and immobilization, with- resulting problems of increased patient susceptibility to complications, and loss of effective reduction with subsequent malunion of disrupted surfaces.

The posterior pelvis is a relatively large weight-bearing portion of the pelvic bone, which transmits proximal weight to the lower limbs. A fracture or dislocation of the posterior pelvis can result in instability in a displacement pattern in a plurality of planes as well as in a rotary direction Thus, posterior pelvic fractures or dislocations are best stabilized and reduced posteriorly, where the frame and pins are proximate to the site of instability and where greater rigidity of fixation may be achieved.

Anterior frames and pins are ineffective in reducing such posterior pelvic fractures, as such frames and pins are remote from the site of the posterior fracture or dislocation, and are not securely affixable thereto. Further, compression applied through such anterior frames in the frontal plane may result in tension and opening of the posterior pelvic fracture, due to the point of application of compressive force relative to the center of rotation of the disrupted posterior pelvic rim.

Still further, such anterior frames and pins are primarily adapted to retain an executed reduction in place, so as to maintain such a reduction already attained, and are generally not capable of providing secure fixation and substantially-anatomic alignment and uniting of surfaces for proper reduction of an unstable posterior pelvic disruption.

SUMMARY OF THE INVENTION

The invention is adapted to overcome the above problems, as well as others, associated with the prior art. It provides an efficient and effective device for enabling substantially-anatomic reduction of a posteriorly unstable pelvic disruption, as of a fracture or dislocation. It further provides such a device for enabling such secure fixation thereof to the posterior pelvis proximate the site of the posterior pelvic disruption.

The device includes a plurality of tapper threaded pins, each adapted to be tapped into the outer cortices of the posterior pelvis at a location proximate the site of the posterior pelvic disruption. Each tapper threaded pin includes an enlarged-diameter, generally truncated-shaped, threaded end, adapted to be securely tapped into the posterior pelvic bone for secure affixation thereof. Each such pin further includes a threaded portion on the shaft thereof proximate the end opposite the threaded end.

The device further includes a frame, adapted to be connectable to the threaded portion of the shaft of each of the tapper threaded pins for connection thereto, and mechanisms, adapted to enable fine adjustment of the frame in a plurality of planes, operable externally of the patient's body. Such externally operable adjustment mechanisms are adapted to apply compressive force, through the securely fixed tapper threaded pins connected thereto, to the posterior pelvis disruption surfaces, for compressing and uniting same into close well-fitting substantially-anatomic engagement, for reduction thereof.

To install the device, first the plurality of tapper threaded pins are tapped into, and threadably secured in, the outer cortices of the posterior pelvis, proximate the site of the disruption with the opposite ends of such pins projecting from the patient's body. The frame is then connected to the projecting end portions of the shafts of the tapper threaded pins, connecting the mechanisms thereto.

To operate the device, the externally-operable mechanisms are operable to adjust the frame so as to apply compressive force through the frame to the tapper threaded pins connected thereto. The tapper threaded pins in turn apply such compressive force, through the outer cortices of the posterior pelvis to which they are securely affixed, in a plurality of planes, to the surfaces of the pelvic disruption, to compress such surfaces into close well-fitting substantially-anatomic union thereof.

The above features of the device enable externally-operable fine adjustment of the posteriorly unstable pelvic disruption surfaces, through the application of compressive force in a plurality of planes, transmitted through the adjustable frame and tapper treaded pins securely affixed to the outer cortices of the posterior pelvis, to effect close well-fitting substantially-anatomic reduction of the posteriorly unstable pelvic disruption. Such features provide rapid and secure stabilization of the posteriorly unstable pelvic disruption, so as to enable prompt patient mobilization, enhancing and speeding up the reduction and healing process, minimizing the chances for complications, and enabling prompt and effective reduction and substantially-anatomical uniting of the disrupted surfaces.

DETAILED DESCRIPTION OF THE INVENTION

Figure 1:
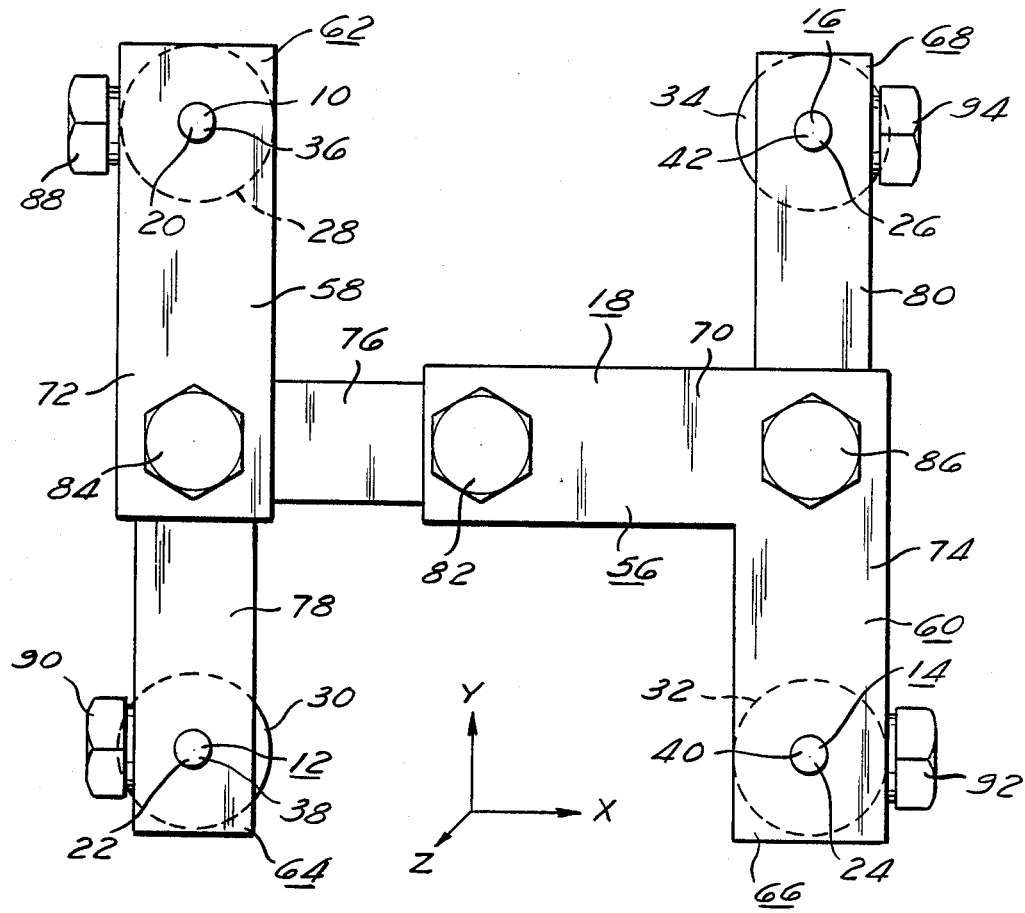
FIG. 1 is a top plan view, in the generally X-Y planes, of a pelvic disruption reducing device, pursuant to the invention.
Figure 2:
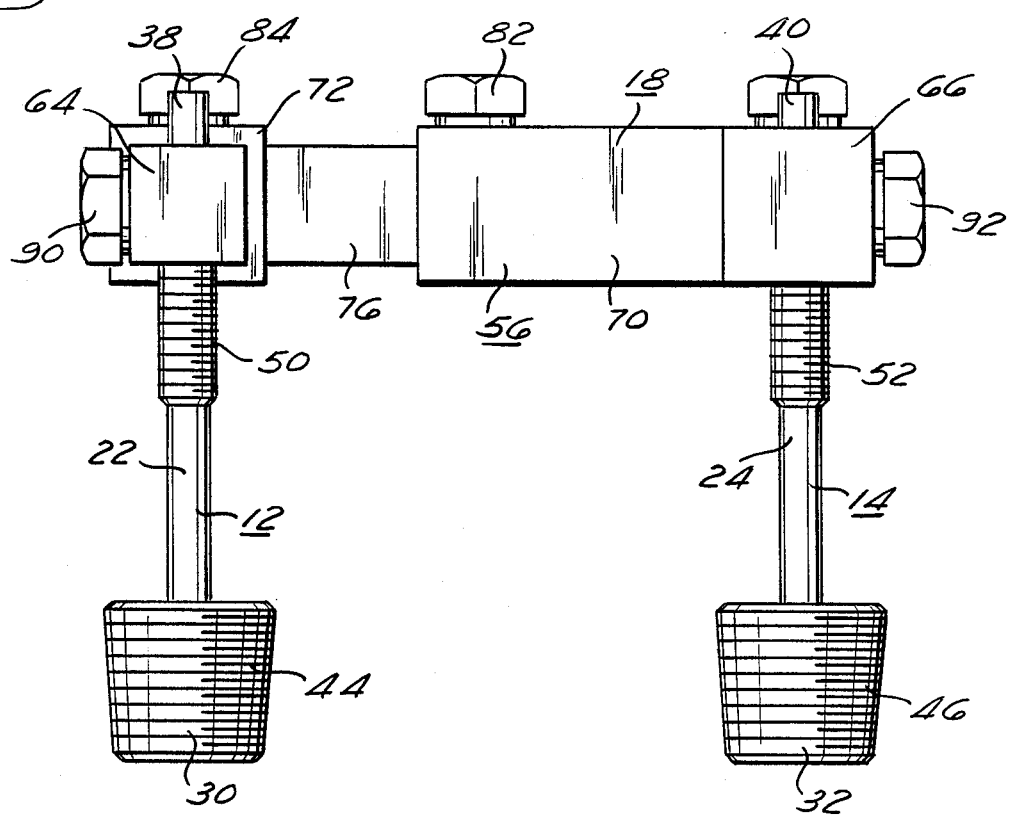
FIG. 2 is a front elevational view, in the generally X-Z plane, of the pelvic disruption reducing device, pursuant to the invention.
Figure 3:
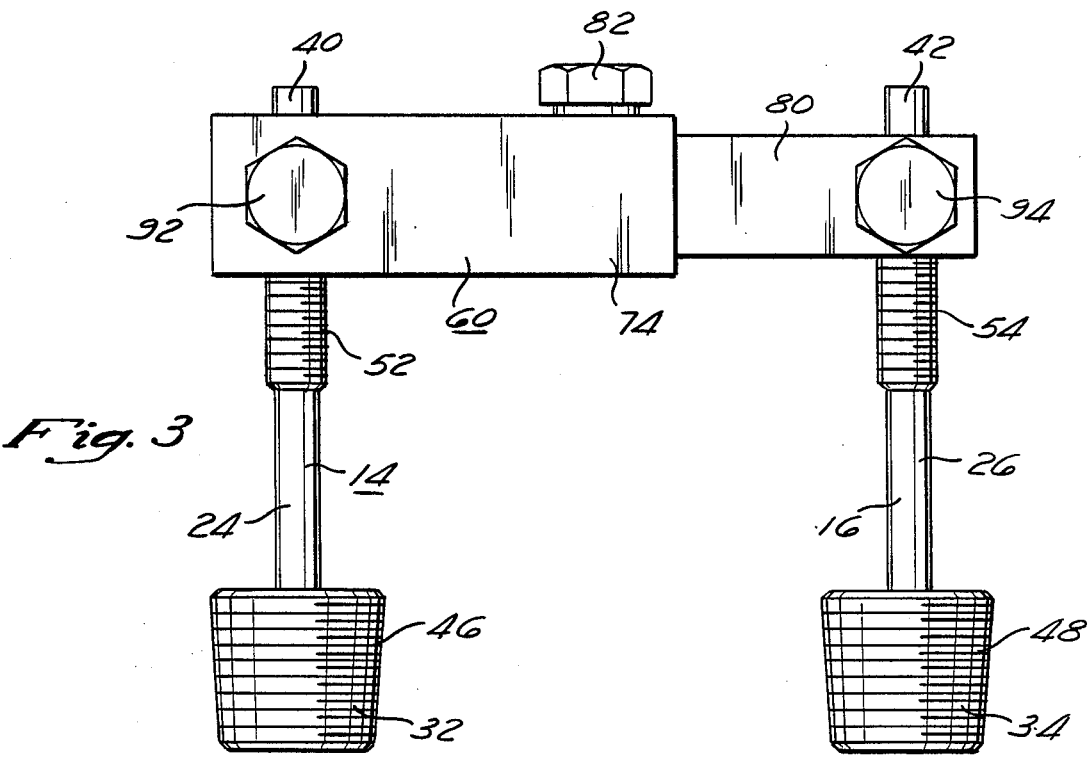
FIG. 3 is a side elevational view, in the generally Y-Z plane, of the pelvic disruption reducing device.

The invention, as shown in FIGS. 1-3, and as described herein, comprises a device for enabling substantially-anatomic reduction of a posteriorly unstable pelvic disruption, as of a fracture of dislocation of the posterior pelvic bone, operable externally of the patient's body. The device further enables secure affixation thereof to the posterior pelvic bone proximate the site of such disruption.

The device includes a plurality of tapper threaded pins, as 10, 12, 14, and 16, adapted to enable secure affixation thereof to the outer cortices of the posterior pelvis proximate the site of the disruption, as shown in FIGS. 1-3.

The device further includes a frame 18, as shown in FIGS. 1-3, adapted to enable connection thereto, and to interconnect, tapper threaded pins 10, 12, 14, and 16, and further adapted to enable fine adjustment thereof, operable externally of the patient's body.

Each tapper threaded pin 10, 12, 14, and 16 is adapted to be tapped into the posterior pelvic bone, and to be connectable to frame 18. Each such pin includes a shaft, as 20, 22, 24, and 26. Each such shaft includes opposed ends, as first end 28, 30, 32, and 34, and as second end 36, 38, 40, and 42.

Each first end 28, 30, 32, and 34 of shafts 20, 22, 24, and 26 is adapted to be tapped into the outer cortices of the posterior pelvis, at a location proximate the site of the posterior pelvic disruption. Each such shaft first end is enlarged, as shown in FIGS. 2-3, the diameter of such first end being larger than the diameter of the shaft. The outer surface of each such first end includes threads, as 44, 46, and 48. Each such first end is generally truncated in shape.

Each such shaft 20, 22, 24, and 26 further includes threads, as 50, 52, and 54, on the outer surface, proximate the second end 36, 38, 40, and 42 thereof.

Frame 18 is adapted to enable each tapper threaded pin 10, 12, 14, and 16 to be connected thereto, and is further adapted to interconnect such tapper threaded pins and to enable fine adjustment of the orientations thereof, to apply compressive force therethrough to the pelvic disruption surfaces and to retain such pins in such positions. It is further adapted to be operable externally of the patient's body.

Frame 18, as shown in FIGS. 1-3, includes a plurality of housings, at least one in each of the planes of adjustment of frame 18, each such housing enabling fine adjustment in its plane of extension and adjustability, as housing 56 in the generally X-plane, FIGS. 1 and 2, housings 58 and 60 in the generally Y-plane, FIGS. 1 and 3, and housings 62, 64, 66, and 68 in the generally Z-plane, FIGS. 1-3. Further adjustable housings may be provided in the rotary or other plane.

Such housings 56, 58, 60, 62, 64, 66, and 68 may include curved portions portions thereof to accommodate curvature of the posterior pelvic bone. Frame 18 further includes pairs of such housings, substantially parallel to each other, in at least one of the plurality of planes, as housings 58 and 60 in the generally Y-plane, and housings 62, 64, 66, and 68 in the generally Z-plane.

Each housing 56, 58, and 60 in the generally X and Y planes includes an outer housing 70, 72, and 74, and an inner housing 76, 78, and 80. Each outer housing 70, 72, and 74 is adapted to be substantially immovable in the plane in which such housing is adapted to be adjustable in, and is generally cylindrical in shape. Each inner housing 76, 78, and 80 is adapted to be movable relative to its corresponding outer housing in the plane in which the housing is adapted to be adjustable, is generally cylindrical in shape, and the diameter thereof is smaller than the diameter of the outer housing for enabling reciprocal slidable movement therein.

Frame 18 further includes control knobs 82, 84, 86, 88, 90, 92, and 94 operable externally of the patient's body, connected through mechanisms (not shown) to the inner housings and tapper threaded pins to enable fine adjustment of the relative positions of such pins. Control knob 82 is connected to inner housing 76 for enabling movement thereof in the generally X-plane. Control knobs 84 and 86 are connected to inner housings 78 and 80 for enabling movement thereof in the generally Y-plane. Control knobs 88, 90, 92, and 94 are connected to threaded portions, as 50, 52, and 54 of tapper threaded pins 10, 12, 14, and 16, for enabling movement thereof in the generally Z-plane. Control knobs 82, 84, 86, 88, 90, 92, and 94 may comprise, for example, hexagonal nuts adapted to be rotated through use of a suitable tool for adjustment of the orientation thereof, to finely adjust the orientations of the housings and to securely retain the positions thereof.

To secure the device in the patient, for enabling reduction of the posteriorly unstable pelvic disruption, the patient is first placed in a position lying face down, and the portion of the body about the posterior pelvic bone is prepared for the procedure. Skin incisions are then made over the sites selected in the posterior pelvic bone for securing the tapper threaded pins.

Holes are then drilled into the outer cortices of the posterior pelvic bone at the selected pin sites, of dimensions sufficient to enable the pins to begin the process of self-tapping into the bone.

Tapper threaded pins 10, 12, 14, and 16 are then inserted into the drilled holes at the selected sites in the posterior pelvis about the site of the posteriorly unstable pelvic disruption. Firm pressure is then exerted on the tapper threaded pins 10, 12, 14, and 16 to self-tap the pins into threaded engagement with the outer cortices of the posterior pelvic bone until the pins are securely engaged in the bone.

In such secured positions of the bone-engaging pins, the threaded, generally truncated-shaped, first end portions 28, 30, 32, and 34 of tapper threaded pins are securely embedded in the outer cortices of the posterior pelvis, and the second end portions 36, 38, 40, and 42 of such pins, including the threaded portions, as 50, 52, and 54 thereof proximate such second ends, project from the patient's body.

Frame 18 is then enagaged with such projecting portions of the pins, externally of the patient's body, by connection thereof to the second ends 36, 38, 40, and 42 of such pins, and particularly to the threaded portions thereof as 50, 52, and 54 proximate such second ends, such that control knobs 88, 90, 92, and 94 of housings 62, 64, 66, and 68 of frame 18, which extend in the generally Z-plane, are engaged with such pins.

To operate the device, upon so securely mounting the device in the patient, fine adjustment of the frame and disruption surfaces in the X, Y, or Z plane is enabled by manipulation of control knobs 82, 84, 86, 88, 90, 92, and 94. Manipulation in the X and Y planes, through control knobs 82, 84, and 86, exerts compressive pressure, through tapper threaded pins 10, 12, 14, and 16 connected thereto through housings 56, 58, 60, 62, 64, 66, and 68, on the surfaces of the pelvic disruption proximate which such pins are secured. Such pressure so exerted compresses and unites the posteriorly unstable pelvic disruption surfaces into close-fitting substantially-anatomic uniting engagement for reducing the disruption.

The above features of the device enable rapid, efficient, and secure stabilization of the posteriorly unstable pelvic disruption, enabling prompt mobilization of the patient without extended bed rest and immobilization, so as to enhance and speed up the healing and reduction process, and prevent complications from arising. Such features further enable fine adjustment of the disruption surfaces into close well-fitting substantially-anatomic engagement thereof, so as to prevent loss of effective reduction and malunion of the disrupted surfaces.

A preferred embodiment of the invention has been set forth above, for the purpose of explaining the invention. However, it is to be understood that variations may be made in such embodiment, which variations are nevertheless within the scope and spirit of the invention as set forth in the claims herein.

I claim:

1. A device for enabling substantially anatomic reduction of an unstable pelvic disruption of the weight transmitting posterior pelvis, securely affixable to the posterior pelvis proximate to the site of the unstable pelvic disruption, and enabling finely adjustable fit of the disrupted surfaces from a position external to a patient's body, so as to compress the posterior pelvic disrupted surfaces into close, well fitting engagement, and to return such surfaces in such engagement for reducing the disruption comprising:
   (a) a plurality of pins disposed in a generally Z plane which is perpendicular to an X axis and a Y axis each of said pins having:
   a shaft having a first end and a second end;
   said first end being adapted to be tapped into the outer corticies of the posterior pelvis at locations proximate to and spaced about the site of the unstable posterior pelvic disruption;
   said second end having threads on the surface of the shaft proximate said second end;
   said first end having a larger diameter than said second end;
   (b) a retaining frame defining a plane having said X axis and said Y axis, including at least one housing along the X axis and at least one housing extending into the Y axis enabling extendability and fine adjustment in the plane of said retaining frame, and further including housings engageable with said second ends of each of said plurality of pins for interconnecting said pins to said retaining frame, enabling fine adjustment in the generally Z plane to apply compressive force therethrough to the posterior pelvic disruption surfaces, to compress and units such disruption surface into close well-fitting engagement, and to retain such surfaces in such engagement, for substantially reducing the unstable posterior pelvic disruption.

2. A device as in claim 1, in which the first end of each pin has the general shape of an inverse truncated cone.

3. A device as in claim 1, in which the frame includes a plurality of housings, at least one such housing in each of the plurality of planes having an externally-operable fine adjustment, each such housing being adapted to be adjustable in one of the plurality of planes, and means for enabling adjustment of the housings in each such plane.

4. A device as in claim 1, in which the frame includes a plurality of housings located in at least one of the plurality of planes having an externally-operable fine adjustment, and means for enabling adjustment of the plurality of housings in such plane.

5. A device as in claim 1, in which the frame includes a pair of substantially parallel housings located in at least one of the plurality of planes having an externally-operable fine adjustment, and means for enabling adjustment of the pair of substantially parallel housings in such plane.

6. A device as in claim 3, in which each housing includes an outer housing, adapted to be substantially immovable in the plane in which such housing is adapted to be adjustable in, and an inner housing, adapted to be movable relative to the outer housing in the plane in which the housing is adapted to be adjustable in.

7. A device as in claim 6, in which the inner housing is adapted to be reciprocally slidably movable relative to the outer housing, in the plane in which the housing is adapted to be adjustable.

* * * * *